United States Patent [19]

Rowles et al.

[11] Patent Number: 4,921,514

[45] Date of Patent: May 1, 1990

[54] MIXED REFRIGERANT/EXPANDER PROCESS FOR THE RECOVERY OF C3+ HYDROCARBONS

[75] Inventors: Howard C. Rowles, Center Valley; Calvin L. Ayres, New Tripoli, both of Pa.

[73] Assignee: Air Products and Chemicals, Inc., Allentown, Pa.

[21] Appl. No.: 351,732

[22] Filed: May 15, 1989

[51] Int. Cl.[5] .................. F25J 3/02

[52] U.S. Cl. .................. 62/24; 62/39

[58] Field of Search .................. 62/24, 38, 39

[56] References Cited

U.S. PATENT DOCUMENTS

| | | | |
|---|---|---|---|
| 4,272,269 | 6/1981 | Hammond et al. | 62/17 |
| 4,272,270 | 6/1981 | Higgins | 62/24 |
| 4,356,014 | 10/1982 | Higgins et al. | 62/28 |
| 4,507,133 | 3/1985 | Khan et al. | 62/29 |
| 4,584,006 | 4/1986 | Apffel | 62/30 |
| 4,666,483 | 5/1987 | Gauthier | 62/24 |
| 4,676,812 | 6/1987 | Kummann | 62/24 |
| 4,705,549 | 11/1987 | Sapper | 62/24 |
| 4,707,170 | 11/1987 | Ayres et al. | 62/24 |
| 4,711,651 | 12/1987 | Sharma et al. | 62/24 |
| 4,714,487 | 12/1987 | Rowles | 62/24 |
| 4,846,863 | 7/1989 | Tomlinson et al. | 62/24 |
| 4,854,955 | 8/1989 | Campbell et al. | 62/24 |

OTHER PUBLICATIONS

D. H. MacKenzie et al., "Mixed Refrigerants Proven Efficient in Natural-Gas-Liquids Recovery Process".

G. R. Daviet et al., "Improving LPG recovery at West Pembina.

*Primary Examiner*—Ronald C. Capossela

*Attorney, Agent, or Firm*—Willard Jones, II; James C. Simmons; William F. Marsh

[57] ABSTRACT

The present invention is an energy efficient process for the recovery and purification of $C_3+$ hydrocarbons from a high pressure natural gas or refinery/petrochemical feed gas containing $C_3+$ hydrocarbons and light gases. In the process, the high pressure feed gas is initially cooled by heat exchange with a multi-component refrigerant fluid circulating in a closed-loop cycle thereby condensing a large portion of the $C_3+$ hydrocarbons. The non-condensed, remaining gas is work expanded to an intermediate pressure thus providing refrigeration for condensing the remaining $C_3+$ hydrocarbons. The condensed $C_3+$ hydrocarbon liquid streams are combined and are further purified by distillation in an integrated distillation column. Optically, refrigeration for refluxing the integrated distillation column can be provided by the mixed refrigerant cycle.

11 Claims, 2 Drawing Sheets

DEPHLEGMATOR

FIRST HEAT EXCHANGER

DISTILLATION COLUMN

DEPHLEGMATOR
FIRST HEAT EXCHANGER
DISTILLATION COLUMN
FIG. I

SECOND
HEAT
EXCHANGER
FIRST HEAT
EXCHANGER
DISTILLATION
COLUMN
30
132
134
137
26
28
22
120
24
18
14
135
62
16
60
58
50
94
102
56
66
96
52
54
12
104
90
100
92
98
68
70
38
63
42
40
10
72
64

MIXED REFRIGERANT/EXPANDER PROCESS FOR THE RECOVERY OF C3+ HYDROCARBONS

TECHNICAL FIELD

The present invention relates to a process for the recovery and purification of $C_3+$ hydrocarbons from a high pressure natural gas or refinery/petrochemical feed gas containing the same.

BACKGROUND OF THE INVENTION

Several processes are known in the art for the recovery and purification of $C_3+$ hydrocarbons. Generally, these processes fall into the following classes:

Expander Processes

These are processes which utilize work expansion of the feed gas, alone or in combination with conventional mechanical refrigeration systems, to recover and purify $C_3+$ hydrocarbons.

Such processes generally involve one or more stages of partial condensation to separate the $C_3+$ hydrocarbons from the lighter components, followed by distillation to remove the $C_2$ and lighter components which have been condensed with the $C_3+$ fraction(s). These processes are relatively inefficient due to the large quantity of $C_2$ and lighter components condensed in the partial condensation stages, particularly at high feed gas pressures, since these light components must subsequently be separated from the $C_3+$ product.

$C_3+$ recovery above about 90% is usually not feasibly due to the limited low temperature refrigeration available from the expander. Auxiliary mechanical refrigeration is usually limited to relatively warm levels, above $-40°$ F., to avoid use of expensive freons, or use of cascade systems which would be necessary for lower temperature refrigeration.

Examples of such processes are disclosed in U.S. Pat. Nos. 4,272,270; 4,356,014 and 4,507,133. A similar expander process is detailed in FIG. 1 of an article by D. H. MacKenzie and S. T. Donnelly in the March 4, 1985 issue of the Oil & Gas Journal, pages 116–120.

Lean Oil Absorption Processes

These processes utilize a heavier hydrocarbon (lean oil) to absorb the $C_3+$ components from the feed gas. U.S. Pat. No. 4,272,269 describes such a process, which utilizes a refrigerated $C_5$ absorption oil to scrub $C_3+$ components from a high pressure natural gas feed which is expanded to an intermediate pressure prior to the absorption step. Mechanical refrigeration is again utilized to supplement the refrigeration provided by the expander.

Such processes are generally of lower energy efficiency than processes which rely primarily on partial condensation of the $C_3+$ components, since the absorbed $C_3+$ components must subsequently be separated from both the heavier lean oil and from the co-absorbed light components. In addition, lean oil losses ($C_5+$) are usually high due to flashing in the overhead of the scrub column. Thermal energy requirements to separate the lean oil from the $C_3+$ products are also high.

Recirculation Processes

A variation of the lean oil absorption process in which a $C_5+$ liquid is mixed with a high pressure feed gas to facilitate condensation of the $C_3+$ components in the feed.

This process is described in an article by G. R. Daviet and N. C. Hircock in the October 21, 1985 issue of the Oil & Gas Journal, pages 74–78. This process is suitable only for relatively lean gases at very high pressures, and for relatively low (70% or less) $C_3$ recovery. As with the lean oil absorption process, it requires separation of the $C_5+$ liquid from the $C_3+$ product for recycle to the feed, in addition to separation of the product $C_3+$ from the co-absorbed light components.

Mixed Refrigerant Processes

These are processes which utilize a refrigeration cycle comprising a mixture of hydrocarbon components to provide the refrigeration necessary to recover and purify the $C_3+$ hydrocarbons. One such process is detailed in FIG. 2 of the above-referenced article by MacKenzie and Donnelly. A similar process is described in U.S. Pat. No. 4,584,006. These processes do not use expanders or dephlegmators.

Such processes are still relatively inefficient since they generally employ the same partial condensation stages used in expander processes, merely substituting a multi-component refrigeration system for the expander and/or conventional mechanical refrigeration systems.

A comparison of the mixed refrigerant process to the expander process is detailed in the article by D. H. MacKenzie and S. T. Donnelly.

A mixed refrigerant process which is particularly suited to recovery of $C_3+$ hydrocarbons from low pressure feed gases is detailed in U.S. Pat. No. 4,707,170.

SUMMARY OF THE INVENTION

The present invention is an improvement to a process for the recovery and purification of $C_3+$ hydrocarbons from a high pressure feed gas stream comprising $C_3+$ hydrocarbons and light gases. In the process, $C_3+$ hydrocarbons are recovered from the feed gas stream by cooling the feed gas stream in heat exchange against a combination of refrigeration sources thereby condensing out the $C_3+$ hydrocarbons. The recovered $C_3+$ hydrocarbons are purified by distillation. The improvement to the process for providing energy efficient refrigeration comprises the following steps.

First, the feed gas stream is cooled whereby a major portion of the $C_3+$ hydrocarbons are condensed and removed from the feed gas stream producing a high pressure, $C_3+$ lean gas stream and a first $C_3+$ hydrocarbon liquid stream. Refrigeration for cooling the feed gas stream and condensing the major portion of the $C_3+$ hydrocarbons is provided in part by heat exchange with a multi-component, closed-loop, refrigerant fluid. The refrigeration provided by the multi-component, closed-loop, refrigerant fluid can be accomplished by operation at two or more different pressure levels.

Second, the high pressure, $C_3+$ lean gas stream is further cooled whereby a second portion of the $C_3+$ hydrocarbons is condensed and removed from the high pressure, $C_3+$ lean gas stream producing an essentially $C_2-$ gas stream and a second $C_3+$ hydrocarbon liquid stream. At least a portion of the refrigeration for the further cooling of the high pressure, $C_3+$ lean gas stream and condensing of the second portion of the $C_3+$ hydrocarbon liquid is provided by work expanding the essentially $C_2-$ gas stream, phase separating the essentially $C_2-$ gas stream thereby producing a third $C_3+$ hydrocarbon liquid stream and a light gas overhead stream, and heat exchanging the light gas overhead stream against the high pressure, $C_3+$ lean gas stream.

Finally, the first, second and third $C_3+$ hydrocarbon liquid streams are combined to form a distillation column feed stream.

The process of the present invention can optionally comprise rectifying the expanded, heat exchanged, essentially $C_2-$ gas stream in a dephlegmator to recover residual $C_3+$ hydrocarbons and combining said residual $C_3+$ hydrocarbons with the first and second $C_3+$ hydrocarbon liquid streams prior to introduction into the distillation column. In such an embodiment, the second step would comprise further cooling the high pressure, $C_3+$ lean gas stream whereby a second portion of the $C_3+$ hydrocarbons is condensed and removed from the high pressure, $C_3+$ lean gas stream thus producing an essentially $C_2-$ gas stream and a second $C_3+$ hydrocarbon liquid stream. At least a portion of the refrigeration for the further cooling of the high pressure, $C_3+$ lean gas stream and condensing the second portion of the $C_3+$ hydrocarbons is provided by work expanding the essentially $C_2-$ gas stream and heat exchanging the expanded, essentially $C_2-$ gas stream against the high pressure, $C_3+$ lean gas stream. This expanded, heat exchanged, essentially $C_2-$ gas stream is then rectified in a dephlegmator to recover residual $C_3+$ hydrocarbons as a third $C_3+$ hydrocarbon liquid stream.

In another embodiment of the dephlegmator process, the second cooling of the high pressure, $C_3+$ lean gas stream is optional. In this case, the second step would comprise work expanding the high pressure, $C_3+$ lean gas stream and phase separating the expanded $C_3+$ lean gas stream thereby producing an essentially $C_2-$ gas stream and a second $C_3+$ liquid hydrocarbon stream. The expanded, essentially $C_2-$ gas stream is then rectified in a dephlegmator to recover residual $C_3+$ hydrocarbons as a third $C_3+$ hydrocarbon liquid stream. The refrigeration for rectification is provided by heat exchange with the expanded, $C_3+$ lean gas stream.

In addition, in either dephlemator embodiment, the expanded, heat exchanged, essentially $C_2-$ gas stream is preferably mixed with one or more of the $C_3+$ hydrocarbon liquid streams prior to rectification in a dephlegmator.

The process of the present invention can also further comprise providing refrigeration for refluxing of the distillation column by heat exchange of the overhead from the distillation column with at least a portion of the multi-component, closed-loop, refrigerant fluid.

DETAILED DESCRIPTION OF THE INVENTION

The present invention is an energy efficient process for the recovery and purification of $C_3$ and heavier liquid hydrocarbons ($C_3+$) from high pressure natural gas streams, or from high pressure refinery/petrochemical type offgas mixtures containing light hydrocarbons ($C_1$ and $C_2$) and/or other light gases, such as $H_2$, $N_2$, CO, and $CO_2$. In particular, the process of the present invention is able to achieve high $C_3$ recovery (90% of more) from feed gases which are initially at pressures of 500 psia or higher, and particularly for feed gases above 700 psia.

The present invention can be best understood in reference to two specific embodiments. These embodiments are illustrated in FIG. 1 and FIG. 2.

Figure 1:
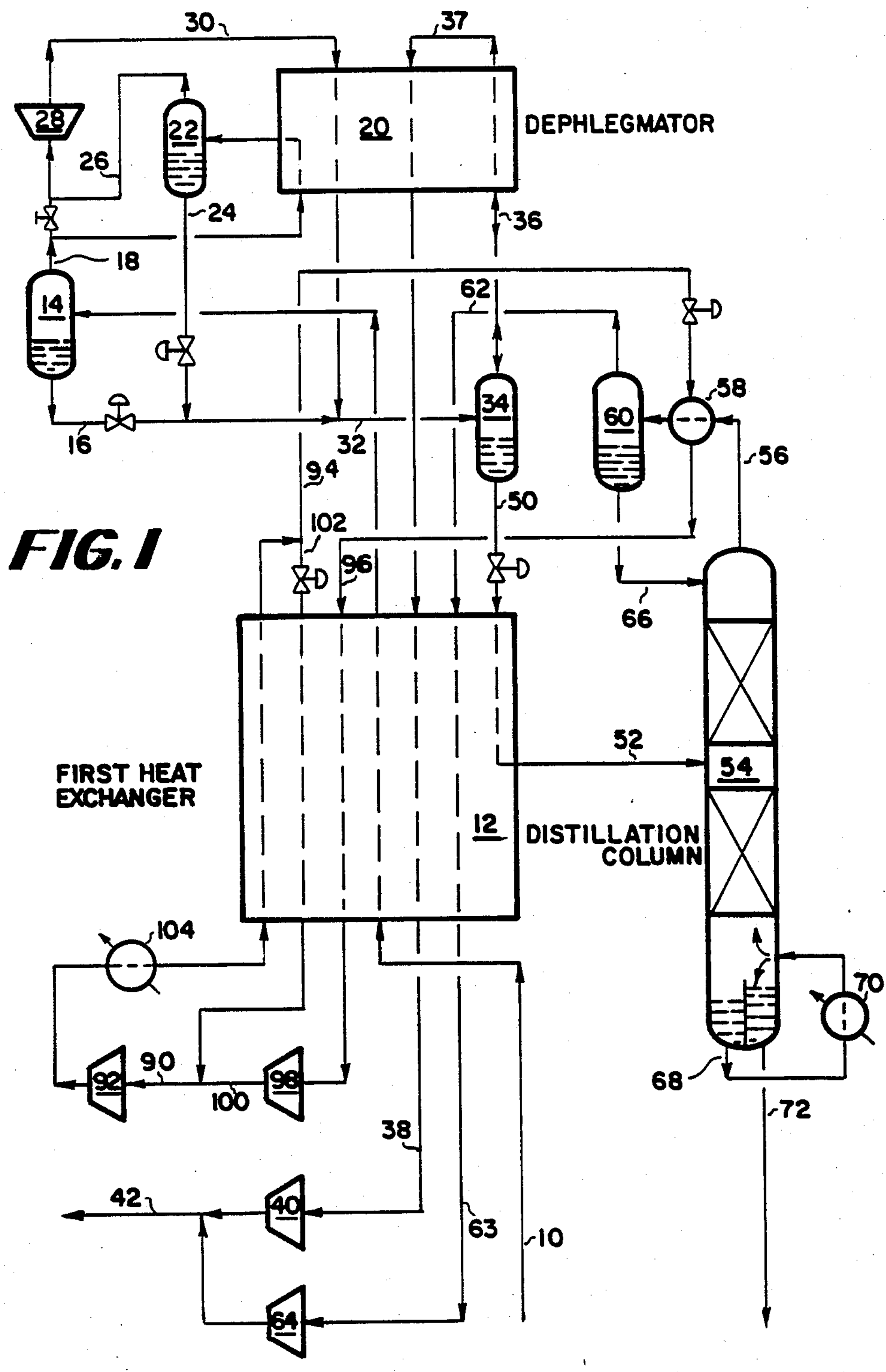
FIG. 1 is a schematic of a first embodiment of the process of the present invention.
Figure 2:
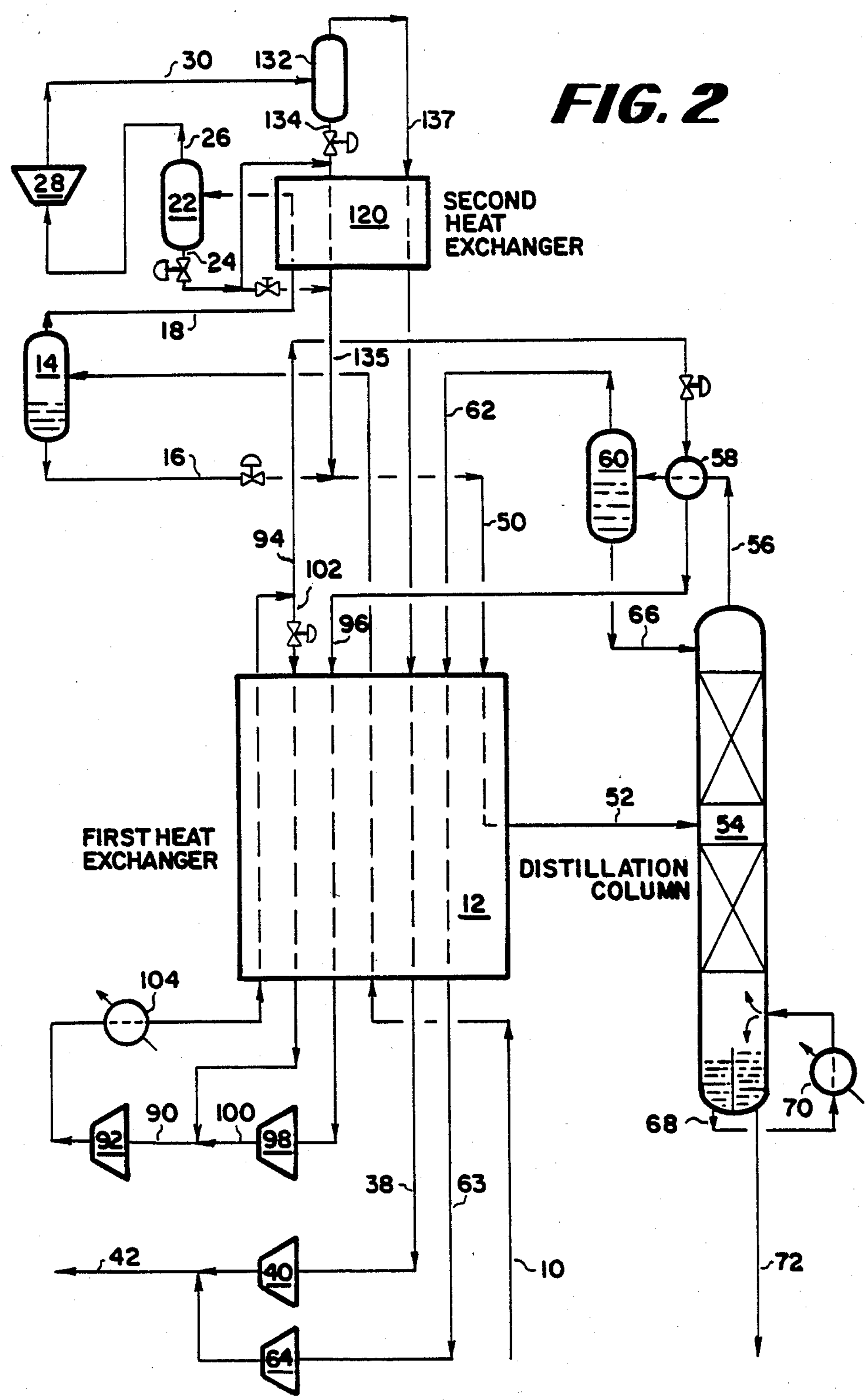
FIG. 2 is a schematic of a second embodiment of the process of the present invention.

With reference to FIG. 1, a single embodiment of the present invention is shown which utilizes a multi-component, closed-loop, refrigerant fluid for refrigeration in the first heat exchanger and feed expansion for refrigeration in the dephlegmator. In the process, a feed gas stream comprising $C_3+$ hydrocarbons and other light gases, e.g., $C_2-$ hydrocarbons and nitrogen, is fed to first heat exchanger 12 via line 10. In first heat exchanger 12, the feed gas is cooled thereby condensing a major portion of the $C_3+$ hydrocarbons. This partially condensed feed stream is then separated in phase separator 14 into a first liquid portion in line 16 and a first vapor portion in line 18. The first vapor portion, in line 18, is then optionally cooled in dephlegmator 20 thereby condensing a further portion of the contained $C_3+$ hydrocarbons. This partially condensed first vapor portion is separated in phase separator 22 into a second liquid portion in line 24 and a second vapor portion in line 26. The second vapor portion is work expanded in expander 28 thereby partially condensing the second vapor portion. This partially condensed second vapor portion is then fed to dephlegmator 20 wherein it is warmed thereby providing refrigeration to the dephlegmator. This warmed vapor is then preferably combined with the first and second liquid portions, in lines 16 and 24, respectively, and fed via line 32 to phase separator 34. In phase separator 34, the combined streams are separated into a column feed liquid stream and an overhead vapor stream.

The overhead vapor stream in line 36 is then fed to dephlegmator 20 wherein it is rectified returning liquid back to phase separator 34 via line 36 as additional column liquid feed. The remaining portion of the overhead stream, in line 37, is then warmed in dephlegmator 20 and first heat exchanger 12 to recover refrigeration and, if necessary, compressed in compressor 40.

The column liquid feed in line 50 is further reduced in pressure (if necessary), warmed and at least partially vaporized in first heat exchanger 12 and fed via line 52 to distillation column 54. The column feed is fractionated therein to produce a column overhead vapor stream in line 56 and bottoms liquid.

The column overhead vapor stream in line 56 is cooled in heat exchanger 58 wherein it is partially condensed. The partially condensed column overhead is then separated in separator 60 into a liquid which is returned to column 54 via line 66 as reflux and a light gas overhead stream in line 62, which is warmed in first heat exchanger 12, compressed in compressor 64, if necessary, and combined with the light gases in line 38 to form the light gas product in line 42.

A portion of the bottoms liquid produced in column 54 is removed via line 68, vaporized in heat exchanger 70 and returned to the bottom of column 54 as reboil. The remaining portion of the bottoms liquid is removed from column 54 via line 72 as the $C_3+$ liquid product.

Refrigeration for heat exchangers 12 and 58 is provided by a multi-component, closed-loop, refrigerant cycle which supplies a large portion of the refrigeration required for the process. The refrigerant mixture, in line 90, is compressed to a suitable pressure in compressor 92, cooled and at least partially condensed with cooling water, air cooling or other suitable means in heat exchanger 104. The compressed refrigerant is further cooled in first heat exchagner 12 and then split into two substreams. The first substream in line 94 is flashed and warmed in heat exchangers 58 and 12, thereby providing refrigeration requirements to heat exchanger 58 and, in part, to heat exchanger 12. The first substream is then compressed in compressor 98, if necessary. The second substream in line 102 is flashed and warmed in heat exchanger 12, thereby providing refrigeration thereto in part. The loop is closed by combining the first substream and the second substream into fluid stream 90.

The process of the present invention is also adaptable to a configuration which does not utilize a dephlegmator. Such an embodiment is shown in FIG. 2; FIGS. 1 and 2 use a common numbering scheme for similar streams and equipment. With reference to FIG. 2, a feed gas stream comprising $C_3$+ hydrocarbons and other light gases, e.g., $C_2$− hydrocarbons and nitrogen, is fed to first heat exchanger 12 via line 10. In first heat exchanger 12, the feed gas is cooled thereby partially condensing a major portion of the $C_3$+ hydrocarbons. This partially condensed feed stream is then separated in phase separator 14 into a first liquid portion in line 16 and a first vapor portion in line 18. The first vapor portion, in line 18, is then further cooled in second heat exchanger 120 thereby condensing a further portion of the contained $C_3$+ hydrocarbons. This partially condensed first vapor portion is separated in phase separator 22 into a second liquid portion in line 24 and a second vapor portion in line 26. The second vapor portion is work expanded in expander 28 thereby partially condensing the second vapor portion. This partially condensed second vapor portion is then phase separated in separator 132 into an overhead stream in line 137 and a liquid stream in line 134. The liquid stream in line 134 is reduced in pressure and optionally combined with the second liquid portion in line 24. This stream is then warmed in second heat exchanger 120 thereby providing refrigeration. This warmed stream in line 135 is then combined with the first liquid portion in line 16 to form a column feed stream in line 50. Alternatively, the liquid stream in line 24 may be warmed separately in second heat exchanger 120 or flashed directly into line 135.

The vapor overhead stream in line 137 is warmed in second heat exchanger 120 and first heat exchanger 12 to recover refrigeration and compressed in compressor 40, if necessary.

The column feed stream in line 50 is warmed and at least partially vaporized in first heat exchanger 12 and fed via line 52 to distillation column 54. The column feed is fractionated therein to produce a column overhead vapor stream in line 56 and bottoms liquid.

The column overhead in line 56 is cooled in heat exchanger 58 wherein it is partially condensed. The partially condensed column overhead is then separated in separator 60 into a liquid which is returned to column 54 via line 66 as reflux and a light gas overhead stream in line 62, which is warmed in first heat exchanger 12, compressed in compressor 64 (if necessary) and combined with the light gases in line 38 to form the light gas product in line 42.

Part of the bottoms liquid produced in column 54 is removed via line 68, vaporized in heat exchanger 70 and returned to the bottom of column 54 as reboil. The remaining portion of the bottoms liquid is removed from column 54 via line 72 as the $C_3$+ liquid product.

Refrigeration for heat exchangers 12 and 58 is provided by a multi-component, closed-loop, refrigerant cycle which supplies a large portion of the refrigeration required for the process. The refrigerant mixture, in line 90, is compressed to a suitable pressure in compressor 92, cooled and at least partially condensed with cooling water, air cooling or other suitable means in heat exchanger 104. The compressed refrigerant is further cooled in first heat exchanger 12 and then split into two substreams. The first substream in line 94 is flashed and warmed in heat exchangers 58 and 12, thereby providing refrigeration requirements to heat exchanger 58 and, in part, to heat exchanger 12. The first substream is then compressed in compressor 98, if necessary. The second substream in line 102 is flashed and warmed in heat exchanger 12, thereby providing refrigeration thereto in part. The loop is closed by combining the first substream and the second substream into fluid stream 90.

In order to demonstrate the efficacy of the present invention, the embodiments shown in FIGS. 1 and 2 were computer simulated. The respective results of these simulations are shown in Tables I and II. Tables I and II are selected stream conditions and compositions for the embodiments of the present invention.

TABLE I

| Stream Number | Temp.: Deg F | Press.: psia | Total Flow: lb-mol/hr | Component Flows: lb-mol/hr N2 | C1 | C2 | C3 | C4+ | |
|---|---|---|---|---|---|---|---|---|---|
| 10 | 100 | 865 | 4087.2 | 966.8 | 2264.8 | 406.6 | 236.9 | 212.1 | |
| 16 | −25 | 860 | 789.3 | 36.3 | 237.8 | 162.2 | 165.5 | 187.5 | |
| 18 | −25 | 860 | 3297.9 | 930.5 | 2027.0 | 244.4 | 71.4 | 24.6 | |
| 24 | −75 | 857 | 279.3 | 19.3 | 124.9 | 71.3 | 43.3 | 20.5 | |
| 26 | −75 | 857 | 3018.6 | 911.2 | 1902.1 | 173.1 | 28.0 | 4.2 | |
| 30 | −113 | 503 | 3018.6 | 911.2 | 1902.1 | 173.1 | 28.0 | 4.2 | |
| 36 | −49 | 500 | 3351.9 | 948.4 | 2101.5 | 237.4 | 52.1 | 12.5 | vapor |
| 36 | −58 | 500 | 123.0 | 3.4 | 30.5 | 34.3 | 42.3 | 12.5 | liquid |
| 38 | 95 | 490 | 3228.9 | 945.0 | 2071.0 | 203.1 | 9.8 | 0.0 | |
| 42 | 98 | 865 | 3638.0 | 966.8 | 2264.8 | 394.6 | 11.8 | 0.0 | |
| 50 | −51 | 500 | 858.3 | 21.8 | 193.8 | 203.5 | 227.1 | 212.1 | |
| 52 | 30 | 360 | 858.3 | 21.8 | 193.8 | 203.5 | 227.1 | 212.1 | |
| 62 | −22 | 350 | 409.1 | 21.8 | 193.8 | 191.5 | 2.0 | 0.0 | |
| 72 | 189 | 350 | 449.2 | 0.0 | 0.0 | 12.0 | 225.1 | 212.1 | |
| 90 | 97 | 87 | 620.0 | 0.0 | 0.0 | 165.0 | 220.0 | 235.0 | |
| 94 | −25 | 255 | 250.0 | 0.0 | 0.0 | 66.5 | 88.7 | 94.8 | |
| 96 | −3 | 23 | 250.0 | 0.0 | 0.0 | 66.5 | 88.7 | 94.8 | |
| 100 | 100 | 87 | 250.0 | 0.0 | 0.0 | 66.5 | 88.7 | 94.8 | |
| 102 | −25 | 255 | 370.0 | 0.0 | 0.0 | 98.5 | 131.3 | 140.2 | |

TABLE II

| Stream Number | Temp.: Deg F | Press.:P psia | Total Flow: lb-mol/hr | Component Flows: lb-mol/hr N2 | C1 | C2 | C3 | C4+ |
|---|---|---|---|---|---|---|---|---|
| 10 | 100 | 865 | 4087.2 | 966.8 | 2264.8 | 406.6 | 236.9 | 212.1 |
| 16 | −25 | 860 | 789.3 | 36.3 | 237.8 | 162.2 | 165.5 | 187.5 |
| 18 | −25 | 860 | 3297.9 | 930.5 | 2027.0 | 244.4 | 71.4 | 24.6 |
| 24 | −80 | 857 | 329.0 | 24.1 | 153.7 | 83.1 | 47.0 | 21.1 |
| 26 | −80 | 857 | 2968.9 | 906.4 | 1873.3 | 161.4 | 24.4 | 3.4 |
| 30 | −103 | 628 | 2968.9 | 906.4 | 1873.3 | 161.4 | 24.4 | 3.4 |
| 137 | −103 | 628 | 2855.0 | 899.4 | 1819.2 | 125.8 | 10.0 | 0.6 |
| 42 | 98 | 865 | 3638.6 | 966.8 | 2264.8 | 394.6 | 11.8 | 0.6 |
| 52 | 25 | 410 | 1232.2 | 67.4 | 445.6 | 280.8 | 226.9 | 211.5 |
| 62 | −36 | 400 | 783.6 | 67.4 | 445.6 | 268.8 | 1.8 | 0.0 |
| 72 | 204 | 400 | 448.6 | 0.0 | 0.0 | 12.0 | 225.1 | 211.5 |
| 90 | 98 | 95 | 730.0 | 0.0 | 0.0 | 205.0 | 260.0 | 265.0 |
| 94 | −25 | 265 | 400.0 | 0.0 | 0.0 | 112.3 | 142.5 | 145.2 |
| 96 | −13 | 20 | 400.0 | 0.0 | 0.0 | 112.3 | 142.5 | 145.2 |
| 100 | 100 | 95 | 400.0 | 0.0 | 0.0 | 112.3 | 142.5 | 145.2 |
| 102 | −25 | 265 | 330.0 | 0.0 | 0.0 | 92.7 | 117.5 | 119.8 |

Alternatives are possible to the prior two embodiments. For example, refrigeration for heat exchanger 58 in the above examples could also be provided at least in part by using expander refrigeration, e.g., a portion of the expanded $C_2^-$ stream in line 30 of FIG. 1 or in line 137 of FIG. 2.

Also, the distillation column of the above embodiments can be operated at a much lower pressure than in the FIG. 1 or 2 examples. In such cases the heat duty for the column reboiler may be supplied by cooling a portion or all of the feed gas, such as in line 10, rather than by an external heat source, such as low pressure steam, and the reflux requirements could be met by using expander refrigeration.

As can be seen from the above description and examples, the key to the present invention is the efficient supply of refrigeration for the process by: (1) revaporizing of a portion of the condensed $C_3$+ liquids in the feed prior to purification in the distillation column; (2) by the expander and (3) by the multi-component, closed-loop, refrigerant cycle. The multi-component, closed-loop, refrigerant cycle is preferably operated with two or more levels of evaporating refrigerant. The composition of the multi-component refrigerant and the pressure levels for revaporization are selected to provide thermodynamically efficient temperature differences between the vaporizing multi-component refrigerant streams and the condensing streams in the first heat exchanger and in the distillation column condenser. The multi-component refrigerant condensing temperature is generally determined by the available cooling medium, such as cooling water, ambient air, or chilled water. In certain situations, it may be possible to condense part or all of the multi-component refrigerant in the reboiler of the distillation column.

Where recompression of the light gas products to high pressure is required, more of the refrigeration is supplied by the multi-component refrigerant cycle, including the refrigeration for the distillation column condenser. This enables the condensed $C_3$+ liquids to be partially revaporized at higher pressure, since less refrigeration is necessary from this source. Thus, the distillation column can be operated at considerably higher pressure, as in the examples of FIGS. 1 and 2, which reduces the power required to recompress the light gas product.

When recompression of the light gas product is not required, refrigeration is shifted to the revaporizing $C_3$+ liquids by flashing the $C_3$+ liquid streams to lower pressure. This requires the distillation column to be operated at lower pressure and temperature, and condenser refrigeration could be supplied by revaporizing $C_3$+ liquids, such as in line 32 or line 50 of FIG. 1 or in line 135 or line 50 of FIG. 2, rather than by the multi-component refrigerant. The compression required for the multi-component refrigerant cycle is therefore reduced.

In all cases, work expansion of the high pressure feed gas is utilized to obtain at least a part of the cold refrigeration required for the process. The amount of refrigeration supplied by the expander is optimized along with the refrigeration supplied by the multi-component refrigerant cycle and by revaporizing $C_3^+$ liquids to minimize the total power requirement of the process.

The dephlegmator is prefered when high $C_3$ recovery, e.g. above 95%, is required, since the rectification achieved in the dephlegmator reduces the quantity of $C_2$ and lighter components which are condensed with the $C_3$+ liquids and must subsequently be removed in the distillation column. It is also prefered to expand the high pressure feed gas to an intermediate pressure, 600 psia or less, prior to dephlegmation. At the lower pressure, the relative volatility between the $C_2^-$ and $C_3^+$ components is higher, and a better separation can be obtained. That is, high $C_3^+$ recovery can be attained with less condensation of light components.

With the partial condensation alternate, the final $C_3^+$ liquid fraction is produced after expansion of the feed gas to intermediate pressure, again to reduce the quantity of light components condensed with the $C_3^+$ hydrocarbons. This alternate is usually favored when lower (95% or less) recovery of $C_3$ is required. The final liquid separation can then be performed at a relatively warmer temperature, which also minimizes condensation of light components.

The process of the present invention, with its combination of the multi-component refrigerant cycle and expander, and, for high $C_3$ recovery, the incorporation of a dephlegmator, results in significant power savings over prior art processes. To illustrate this savings, the embodiments of FIGS. 1 and 2, which have a total power requirement for 95% $C_3$ recovery and recompression of the light gases to feed pressure of 1688 and 1596 HP, respectively, were compared to two prior art processes. For a conventional prior art expander process (such as disclosed in FIG. 1 of MacKenzie, et al.), using a single component ($C_3$) refrigeration cycle for auxiliary refrigeration, the total power requirement was found to be 2362 HP. For a recirculation (absorption)

process (such as disclosed in Daviet, et al.), the total power requirement was 2257 HP. Thus, the process of this invention requires about 30% less power than these prior art processes.

The present invention has been described in reference to several specific embodiments thereof. These embodiments should not be viewed as a limtation of the scope of the present invention. Such scope should be ascertained by the following claims.

We claim:

1. In a process for the recovery and purification of $C_3+$ hydrocarbons from a high pressure feed gas stream comprising $C_3+$ hydrocarbons and light gases wherein the $C_3+$ hydrocarbons are recovered from the feed gas stream by cooling the feed gas stream in heat exchange against a combination of refrigeration sources thereby condensing out the $C_3+$ hydrocarbons and wherein the recovered $C_3+$ hydrocarbons are purified by distillation, the improvement for providing energy efficient refrigeration comprises:

(a) cooling the feed gas stream whereby a major portion of the $C_3+$ hydrocarbons are condensed and removed from the feed gas stream thus producing a high pressure, $C_3+$ lean gas stream and a first $C_3+$ hydrocarbon liquid stream; wherein refrigeration for cooling the feed gas stream and condensing the major portion of the $C_3+$ hydrocarbons is provided in part by heat exchange with a multi-component, closed-loop, refrigerant fluid;

(b) further cooling the high pressure, $C_3+$ lean gas stream whereby a second portion of the $C_3+$ hydrocarbons is condensed and removed from the high pressure, $C_3+$ lean gas stream thus producing an essentially $C_2-$ gas stream and a second $C_3+$ hydrocarbon liquid stream; wherein at least a portion of the refrigeration for the further cooling of the high pressure, $C_3+$ lean gas stream and condensing the second portion of the $C_3+$ hydrocarbons is provided by work expanding the essentially $C_2-$ gas stream, phase separating the expanded, essentially $C_2-$ gas stream thereby producing a third $C_3+$ hydrocarbon liquid stream and a light gas overhead stream and heat exchanging the light gas overhead stream against the high pressure, $C_3+$ lean gas stream; and (c) combining the first, second and third $C_3+$ hydrocarbon liquid streams to form a distillation column feed stream, warming and at least partially vaporizing the distillation column feed stream and introducing the distillation column feed stream into an intermediate location of the distillation column.

2. The process of claim 1 which further comprises providing refrigeration for refluxing of the distillation column by heat exchange of the overhead from the distillation column with at least a portion of the multi-component, closed-loop, refrigerant fluid.

3. The process of claim 1 wherein the refrigeration provided by the multi-component, closed-loop, refrigerant fluid is accomplished at two or more different pressure levels.

4. In a process for the recovery and purification of $C_3+$ hydrocarbons from a high pressure feed gas stream comprising $C_3+$ hydrocarbons and light gases wherein the $C_3+$ hydrocarbons are recovered from the feed gas stream by cooling the feed gas stream in heat exchange against a combination of refrigeration sources thereby condensing out the $C_3+$ hydrocarbons and wherein the recovered $C_3+$ hydrocarbons are purified by distillation, the improvement for providing energy efficient refrigeration comprises:

(a) cooling the feed gas stream whereby a major portion of the $C_3+$ hydrocarbons are condensed and removed from the feed gas stream thus producing a high pressure, $C_3+$ lean gas stream and a first $C_3+$ hydrocarbon liquid stream; wherein refrigeration for cooling the feed gas stream and condensing the major portion of the $C_3+$ hydrocarbons is provided in part by heat exchange with a multi-component, closed-loop, refrigerant fluid;

(b) further cooling the high pressure, $C_3+$ lean gas stream whereby a second portion of the $C_3+$ hydrocarbons is condensed and removed from the high pressure, $C_3+$ lean gas stream thus producing an essentially $C_2-$ gas stream and a second $C_3+$ hydrocarbon liquid stream; wherein at least a portion of the refrigeration for the further cooling of the high pressure, $C_3+$ lean gas stream and condensing the second portion of the $C_3+$ hydrocarbons is provided by work expanding the essentially $C_2-$ gas stream and heat exchanging the expanded, essentially $C_2-$ gas stream against the high pressure, $C_3+$ lean gas stream;

(c) rectifying the expanded, heat exchanged, essentially $C_2-$ gas stream in a dephlegmator to recover residual $C_3+$ hydrocarbons as a third $C_3+$ hydrocarbon liquid stream; and (d) combining the first, second and third $C_3+$ hydrocarbon liquid streams to form a distillation column feed stream, warming and at least partially vaporizing the distillation column feed stream and introducing the distillation column feed stream into an intermediate location of the distillation column.

5. The process of claim 4 which further comprises providing refrigeration for refluxing of the distillation column by heat exchange of the overhead from the distillation column with at least a portion of the multi-component, closed-loop, refrigerant fluid.

6. The process of claim 4 wherein the refrigeration provided by the multi-component, closed-loop, refrigerant fluid is accomplished at two or more different pressure levels.

7. The process of claim 4 which further comprises mixing one or more of the $C_3+$ hydrocarbon liquid streams with the expanded, essentially $C_2-$ gas stream prior to rectification in the dephlegmator.

8. In a process for the recovery and purification of $C_3+$ hydrocarbons from a high pressure feed gas stream comprising $C_3+$ hydrocarbons and light gases wherein the $C_3+$ hydrocarbons are recovered from the feed gas stream by cooling the feed gas stream in heat exchange against a combination of refrigeration sources thereby condensing out the $C_3+$ hydrocarbons and wherein the recovered $C_3+$ hydrocarbons are purified by distillation, the improvement for providing energy efficient refrigeration comprises:

(a) cooling the feed gas stream whereby a major portion of the $C_3+$ hydrocarbons are condensed and removed from the feed gas stream thus producing a high pressure, $C_3+$ lean gas stream and a first $C_3+$ hydrocarbon liquid stream; wherein refrigeration for cooling the feed gas stream and condensing the major portion of the $C_3+$ hydrocarbons is provided in part by heat exchange with a multi-component, closed-loop, refrigerant fluid;

(b) work expanding the high pressure, $C_3+$ lean gas stream and phase separating the expanded $C_3+$ lean gas stream thereby producing an essentially $C_2^-$ gas stream and a second $C_3^+$ liquid hydrocarbon stream;

(c) rectifying the expanded, essentially $C_2^-$ gas stream in a dephlegmator to recover residual $C_3^+$ hydrocarbons as a third $C_3^+$ hydrocarbon liquid stream, wherein refrigeration for rectification is provided by heat exchange with the expanded, $C_3^+$ lean gas stream; and (d) combining the first, second and third $C_3^+$ hydrocarbon liquid streams to form a distillation column feed stream, warming and at least partially vaporizing the distillation column feed stream and introducing the distillation column feed stream into an intermediate location of the distillation column.

9. The process of claim 8 which further comprises providing refrigeration for refluxing of the distillation column by heat exchange of the overhead from the distillation column with at least a portion of the multi-component, closed-loop, refrigerant fluid.

10. The process of claim 8 wherein the refrigeration provided by the multi-component, closed-loop, refrigerant fluid is accomplished at two or more different pressure levels.

11. The process of claim 8 which further comprises mixing one or more of the $C_3^+$ hydrocarbon liquid streams with the expanded, essentially $C_2^-$ gas stream prior to rectification in the dephlegmator.

* * * * *